United States Patent [19]
Felder et al.

[11] Patent Number: 5,695,742
[45] Date of Patent: Dec. 9, 1997

[54] AQUEOUS INJECTABLE FORMULATIONS USEFUL FOR RADIODIAGNOSIS COMPRISING IODINATED AROMATIC COMPOUNDS USED AS X-RAY CONTRAST MEDIA

[75] Inventors: Ernst Felder; Christoph de Haen, both of Milan, Italy

[73] Assignee: Dibra S.p.A., Milan, Italy

[21] Appl. No.: 448,509

[22] PCT Filed: Dec. 20, 1993

[86] PCT No.: PCT/EP93/03613

§ 371 Date: May 25, 1995

§ 102(e) Date: May 25, 1995

[87] PCT Pub. No.: WO94/14478

PCT Pub. Date: Jul. 7, 1994

[30] Foreign Application Priority Data

Dec. 24, 1992 [IT] Italy ............... MI92A2964

[51] Int. Cl.$^6$ ............... A61K 49/00; G01N 31/00; G01N 33/48
[52] U.S. Cl. ............... 424/9.455; 424/9.45; 424/9.4; 424/9.1
[58] Field of Search ............... 424/9.454, 9.455, 424/1.11, 9.1, 9.4, 9.42, 9.45, 9.451

[56] References Cited

U.S. PATENT DOCUMENTS

| | | | |
|---|---|---|---|
| 2,613,172 | 10/1952 | Galler | 424/9.45 |
| 4,001,323 | 1/1977 | Felder et al. | 424/9.454 |
| 4,474,747 | 10/1984 | Dimo et al. | 424/1.11 |
| 5,075,502 | 12/1991 | Kneller et al. | 424/9.44 |
| 5,191,120 | 3/1993 | Kneller et al. | 564/153 |
| 5,260,478 | 11/1993 | Bacon et al. | 424/9.45 |
| 5,328,680 | 7/1994 | Almen et al. | 424/9.454 |
| 5,366,722 | 11/1994 | Almen et al. | 424/9.452 |
| 5,384,107 | 1/1995 | Singh et al. | 424/9.45 |

FOREIGN PATENT DOCUMENTS

| | | |
|---|---|---|
| 0390242 | 3/1990 | European Pat. Off. |
| 2050167 | 1/1981 | United Kingdom |
| 9113636 | 9/1991 | WIPO |
| 9405337 | 3/1994 | WIPO |
| 9414478 | 7/1994 | WIPO |

OTHER PUBLICATIONS

Priebe et al (1995) Acta Chem. Scand. vol. 49, No. 10, pp. 737–743. "Synthesis, analysis, and toxicity of three compounds formed during the synthesis of iodixanol".

Lin et al (1994), Invest. Radiol., vol. 29, Suppl. 2, pp. S275–S277. "New ionic triiodinated X-ray contrast media containing the N-(2-hydroxy-ethyl)amino propane-2, 3-diol side chain".

Pavone et al (1990). Radiology, vol. 176, No. 1, pp. 61–64. Comparison of Gd–BOPTA with Gd–DTPA in MR Imaging of Rat Liver.

Smed by (1992). Acta. Radiologica, vol. 33, Fasc. 6, pp. 660–605. "Viscosity of Some Contemporary Contrast Media Before and After Mixing with Whole Blood".

*Primary Examiner*—John Kight
*Assistant Examiner*—Dameron Jones
*Attorney, Agent, or Firm*—Bucknam and Archer

[57] ABSTRACT

This invention refers to injectable aqueous formulations containing radiopaque contrast agents useful for X-ray imaging of human or animal body. This invention specially deals with injectable aqueous solutions of mixtures of non-ionic and water-soluble iodinated aromatic compounds preferably constituted by: a) compounds comprising an aromatic nucleus at least triiodo-substituted; b) compounds comprising at least two aromatic nuclei variably bound together, each one at least triiodo substituted.

5 Claims, No Drawings

AQUEOUS INJECTABLE FORMULATIONS USEFUL FOR RADIODIAGNOSIS COMPRISING IODINATED AROMATIC COMPOUNDS USED AS X-RAY CONTRAST MEDIA

FIELD OF THE INVENTION

This invention refers to injectable aqueous formulations containing radiopaque contrast agents useful for X-ray imaging of human or animal body.

One of the preferred aspects of this invention specially deals with injectable aqueous solutions of mixtures of non-ionic and water-soluble iodinated aromatic compounds preferably constituted by:

a) compounds comprising an aromatic nucleus at least triiodo-substituted—from now on referred to as monomers or monomeric, b) compounds comprising at least two aromatic nuclei variably bound together, each one at least triiodo substituted—from now on referred to as dimers or dimeric.

Beyond the compounds of type a) and b), this invention also includes other possible mixtures comprising opacifying derivatives with molecular structures of three or more polyiodinated aromatic nuclei.

BACKGROUND OF THE INVENTION

Formulations containing X-ray contrast agents (CM) have long been used to enhance the image contrast of human and animal cavities in X-ray examinations. Among the past radiopaque products which have been investigated, it is worth mentioning derivatives of elements such as Ba, Bi, Ta. But afterwards it was found that certain classes of water-soluble brominated and/or iodinated organic compounds are far greatly useful as contrast agents for the vascular system.

2,4,6-triiodo-benzene derivatives are commonly used as iodinated aromatic X-ray-opaque compounds since their remaining positions 1,3,5 are substituted by suitable organic substituents to reach a sufficient watersolubility, a iodine concentration of 300–450 g/L or more, and a good tolerability.

A good solubility, for example, can be obtained through the introduction on the aromatic nucleus of carboxylic functions which can be salified. These compounds are the so-called ionic iodinated contrast agents. A typical example is the diatrizoic acid (3,5-diacetamido-2,4,6-triiodobenzoic acid) and its meglumine salt, particularly used in angiography. It is highly water-soluble and has a relatively low molecular weight. These features allow injectable solutions with a high iodine content and a low viscosity, essential for a good vascular X-ray imaging.

Unfortunately, ionic contrast media solutions show a high toxicity. Furthermore they are hyperosmotic to plasma (the presence of ions considerably increases osmolality and therefore the osmotic pressure when compared to other physiological fluids), causing possible painful effects in patients after injection. Other drawbacks related to ionic contrast agents rely on the presence of massive counter-cation concentrations ($Na^+$, $Ca^{2+}$ and others): the consequence is an increase in the osmotic load, that's to say the amount of administered osmoles, pro dose. It is known that a high osmotic load causes a toxicity increase. Moreover cardiovascular effects may occur as a result of the increase in plasma volume.

To overcome this problem, non-ionic iodinated agents have been developed, where the substituents on the aromatic nucleus have no ionizable functions. In this case a sufficient water-solubility is granted by highly hydrophilic neutral groups in positions 1,3,5 of the aromatic nucleus. Non-limiting examples of compounds belonging to this last mentioned class of opacifying agents are given by "iopamidol" (BRACCO), or N,N'-bis-[2-hydroxy-1-(hydroxymethyl)ethyl]-2,4,6-triiodo-5-lactamido-isophthalamide, and "iomeprol" (BRACCO) or N,N'-bis-(2,3-dihydroxypropyl)-2,4,6-triiodo-5-(N-methyl-hydroxyacetyl amino)-isophthalamide.

Disregarding the improvements obtained on non-ionic aromatic triiodo-derivatives, there was still the need of decreasing the osmolality in the corresponding opacifying injectable formulations in order to obtain an osmotic pressure more similar to blood. Osmolality is the common term used to relate molality to osmotic pressure. In fact, highly concentrated solutions of different iododerivatives, can show osmolality values that are too high to be tolerable by the human body. By way of an example, a 1 osmol/kg. $H_2O$ (=1000 mosmol/kg) solution can generate a 25.5-atm or 2.58-MPa osmotic pressure, hence a physiologically unacceptable value. A way to decrease osmolality, by keeping the total iodine content of aqueous solutions between a desired range, is favouring molecular aggregation. Another way consists in increasing the number of atoms of iodine per molecule, for instance by covalently binding together two or more triiodinated aromatic nuclei through suitable alkylenic bridges, functionally substituted or not, to obtain the so-called oligomeric or dimeric structures. However in this case, the viscosity of said compounds usually reaches values scoring more than 8–14 mPa7s. This range is generally considered the highest acceptable limit for catheter administrations of opacifying solutions at a rate compatible with the vascular system imaging.

Referring, to the above mentioned problems, a wide bibliographic documentation is available comprising technical articles, patents and books. Quite useful documents can be: "X-Ray Contrast Media", by U. Speck published by Medical Division, Department of Medical Information, Schering AG (DE); D. P. Swanson et al., "Pharmaceuticals in Medical Imaging" (1990) Mc Millan Publ. Co.; "Radio-contrast Agents", by M. Sovak, published by Springer Verlag (1984), M. Elke et al., "Kontrastmittel in der radiologischen Diagnostik", G. Thieme Verlag Stuttgart, New York (1992).

Table 1 reports data, disclosed in the prior art, of some well-known iodinated contrast agents, considering the corresponding osmolality and viscosity values of their aqueous solutions according to certain iodine concentrations. Letters i, ni, m, d, stand for compound structural characteristics (i—ionic; ni—non ionic; m—monomer; d—dimer).

TABLE 1

| Compound or medium solution | Structure | Iodine (g/L) | Osmolality H$_2$O mosmol/kg | Viscosity at 37° C. (mPa · s) |
|---|---|---|---|---|
| Blood | — | — | 290 | 4 |
| diatrizoate (meglumine) | i m | 282 | 1500 | 4 |
| ioxaglate | i d | 320 | 580 | 7.5 |
| iopromide | ni m | 300 | 630 | 4.6 |
| iopamidol | ni m | 300 | 620 | 4.5 |
| iomeprol | ni m | 300 | 521 | 4.5 |
| iohexol | ni m | 300 | 690 | 6.1 |
| metrizamide | ni m | 300 | 485 | 6.2 |
| ioversol | ni m | 320 | 702 | 5.8 |
| iogulamide | ni m | 300 | 1040 | 9.6 |
| iodixanol | ni d | 300 | 200 | 8.7 |
| iodecol | ni d | 300 | 320 | 7.2 |
| iotrol | ni d | 300 | 320 | 8.1 |
| iofratol | ni d | 300 | 141 | 8.5 |
| EP-23992 B (compound A, Ex. 15) | ni d | 300 | 184 | 7.4 |

The data of Table 1 show that, osmolality levels are still too high if compared to blood (about 300 mosmol/kg), despite the shift from ionic to non-ionic contrastographic compounds which remarkably reduces the injectable solution osmolality if a iodine concentration of about 300 g/L is used. A way to further reduce osmolality, down to the blood value or even lower values, is using iodinated compounds such as dimers. But, on the other hand, viscosity is too high for most of diagnostic applications requiring quick injections of opacifying formulations into the vascular system. It is worth remembering that in the X-ray vascular imaging, iodine delivery rate is very important. The rate is expressed in grams of iodine per second at 370C. [g(iodine)/s], meanwhile the injection pressure through less invasive catheters (i.e. Cordis.4F) is of about 61.2 atm or 6.20 MPa. Obviously, iodine delivery rate depends on the solution concentration and on the volumetric flow rate, which is connected to viscosity and the kind of flow.

Furthermore, in some cases, dimeric solutions are hypotonic and this requires a salt addition to their formulations to reach the isotonicity with blood.

Patent application GB-A-2050167 (Mallinckrodt) claims that it is possible obtaining X-ray opacifying compositions that, at a iodine concentration of 34–40% in weight, have a viscosity lower than 9–10 mPa's at 370° C., when solutions containing mixtures of ionic and non-ionic iodinated contrast agents are prepared. But as a matter of fact, this approach does not overcome the above mentioned difficulties since the neutralisation of counter-cations is still necessary. The results is an increase in osmolality and the osmotic load, despite the acceptable viscosity values possibly obtained.

Other documents which can be cited as a reference to the state of the art are: U.S. Pat. No. 3,701,771, U.S. Pat. No. 4,396,598, U.S. Pat. No. 5,019,271, WO 92/09562, WO 92/13636, WO 89/08101, EP 390242, EP 437444, EP 306364. Nevertheless none of them gives a satisfactory answer to the above disclosed problems.

SUMMARY OF THE INVENTION

This invention provides important and significant advantages in the field of injectable formulations of iodinated contrast media for X-ray imaging. It was unexpectedly and surprisingly found that injectable aqueous compositions, comprising mixtures of non-ionic iodinated aromatic compounds monomer of type (a) and dimers of type (b), not only have an intermediate osmolality compared to the pure solutions of (a) and (b), and are also isoosmolal or isotonic to the plasma but they also have a lower viscosity than the expected, and a lower toxicity than those shown by the corresponding pure solutions of (a) and (b). Furthermore, during the injection, they supply a favourable iodine delivery rate through less invasive catheters.

Compounds (a) preferably have a structure as indicated in the following general formula (I)

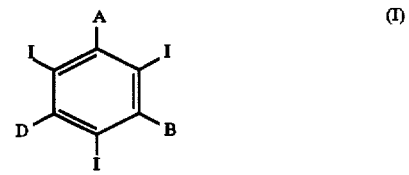

wherein:

A, B, D, which are the same or different, are —CON(R)R$_1$ or —N(R)—CO—R$_2$ groups, wherein R is H or a linear or branched alkyl residue (C$_1$–C$_6$), optionally substituted by 1–5 OH and/or alkoxy and/or hydroxyalkoxy groups, R$_1$ is a linear or branched alkyl residue (C2–C$_6$), optionally substituted by 1–5 OH and/or alkoxy and/or hydroxyalkoxy groups, or by one of the two groups —NH—CO—R$_1$ or —CO—N (R)R$_1$, or R$_1$ is the residue of a carbohydrate, or R$_1$ and R, taken together, are an alkylene chain (C3–C$_7$) which can be interrupted by O, S, N, R$_2$ is a linear or branched alkyl residue (C1–C$_6$), optionally substituted by 1–5 OH and/or alkoxy and/or hydroxyalkoxy groups, and can also include an oxo group.

Compounds (b) preferably have the following formula (II)

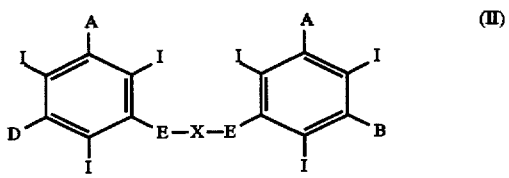

wherein:

A, B, D, which are the same or different, have the same meanings of formula I,

E, which are the same or different, are selected among —CO—N(R)—, —N(R)—CO—, —N(COR$_3$)— groups where R has the same meanings of formula (I) and R$_3$ is an alkyl residue ($C_1$-$C_3$) optionally substituted by 1–2 OH or by alkoxy or hydroxyalkoxy groups, X is a covalent bond or a linear or branched alkylene chain ($C_1$-$C_8$), which can be substituted by 1–6 OH groups and/or —CO—NHR groups, and which can be interrupted by —O—, —S—, —N—, —N(R)—CO groups, being R as above defined in formula (I).

Among monomers of type (a), particularly preferred are those listed in Table 2.

TABLE 2

Preferred compound of type (a)

| Generic Name (source) CAS [RN] | A | B | D |
|---|---|---|---|
| metrizamide [31112-62-6] | —CONHCH(CHOH)$_3$CH$_2$OH<br>\|<br>CHO | —N(Me)Ac | —NH—Ac |
| iopamidol [60166-93-0] | —CONHCH(CH$_2$OH)$_2$ | —CONHCH(CH$_2$OH)$_2$ | —NHCOCH(OH)CH$_3$ |
| iomeprol [78649-41-9] | —CONCH$_2$CH(OH)CH$_2$OH | —CONCH$_2$CH(OH)CH$_2$OH | —N(Me)COCH$_2$OH |
| iopromide [73334-07-3] | —CONCH$_2$CH(OH)CH$_2$OH | —CONCH$_2$CH(OH)CH$_2$OH<br>\|<br>Me | —NHCOCH$_2$OMe |
| ioversol [877771-40-2] | —CONCH$_2$CH(OH)CH$_2$OH | —CONCH$_2$CH(OH)CH$_2$OH | —N—COCH$_2$OH<br>\|<br>CH$_2$CH$_2$OH |
| iohexol [66108-95-0] | —CONCH$_2$CH(OH)CH$_2$OH | —CONCH$_2$CH(OH)CH$_2$OH | —N—Ac<br>\|<br>CH$_2$CH(OH)CH$_2$OH |
| iopentol [89797-00-2] | —CONCH$_2$CH(OH)CH$_2$OH | —CONCH$_2$CH(OH)CH$_2$OH | —N—Ac<br>\|<br>CH$_2$CH(OH)CH$_2$OMe |
| ioxilan [107793-72-6] | —CONCH$_2$CH$_2$OH | —CONCH$_2$CH(OH)CH$_2$OH | —N—Ac<br>\|<br>CH$_2$CH(OH)CH$_2$OH |
| II-1 [99139-49-8] | —CONCH$_2$CH(OH)CH$_2$OH | —N—Ac<br>\|<br>CH$_2$CH(OH)CH$_2$OH | —N—Ac<br>\|<br>CH$_2$CH(OH)CH$_2$OH |
| iogulamide [75751-89-2] | —CONHCH$_2$CH(OH)CH$_2$OH | —CONCH$_2$CH(OH)CH$_2$OH | —NHCOCO(CHOH)$_3$CH$_2$OH |
| ioglucol [63941-73-1] | —CONHMe | —NHCOCH(OH)$_4$CH$_2$OH | —N—Ac<br>\|<br>CH$_2$CH$_2$OH |
| ioglucamide [63941-74-2] | —CONHMe | —NHCOCH(OH)$_4$CH$_2$OH | —NHCOCHOH)$_4$CH$_2$OH |
| ioglunide [56562-79-9] | —CONHCH$_2$CH$_2$OH | —NHCOCH(OH)$_4$CH$_2$OH | —N(Me)Ac |
| MP-7011 [76984-84-0] | —CONHCH$_2$(CHOH)$_5$CH$_2$OH | —N(Me)Ac | —NH—Ac |
| MP-7012 [64965-50-0] | —CONHCH$_2$CONHCH(CHOH)$_3$CH$_2$OH<br>\|<br>CH$_2$OH | —N(Me)Ac | —NH—Ac |
| MP-10007 [77111-65-0] | —CONHCH$_2$CH$_2$OH | —NHCOCO(CHOH)$_3$CH$_2$OH | —NHCOCO(CHOH)$_3$CH$_2$OH |
| VA-7-88 [79944-49-3] | —CONHCHCH(OH)CH$_2$OH<br>\|<br>CH$_2$OH | —CONHCHCH(OH)CH$_2$OH<br>\|<br>CH$_2$OH | —N(Me)Ac |
| (EP 033426) [79944-51-7] | —CONHCHCH(OH)CH$_2$OH<br>\|<br>CH$_2$OH | —CONHCHCH(OH)CH$_2$OH<br>\|<br>CH$_2$OH | —CONHCHCH(OH)CH$_2$OH<br>\|<br>CH$_2$OH |
| iosimide [79211-10-2] | —CON(CH$_2$CH$_2$OH)$_2$ | —CON(CH$_2$CH$_2$OH)$_2$ | —CON(CH$_2$CH$_2$OH)$_2$ |
| iocibidol [79211-34-0] | —CONCH$_2$CH(OH)CH$_2$OH<br>\|<br>Me | —CONHCH$_2$CHCH$_2$OH<br>\|<br>OH | —CONH$_2$ |

TABLE 2-continued

Preferred compound of type (a)

| Generic Name (source) CAS [RN] | FORMULA I | | |
|---|---|---|---|
| | A | B | D |
| (EP 0177414) [103876-29-5] | —N—Ac<br>\|<br>CH$_2$CH(OH)CH$_2$OH | —N—Ac<br>\|<br>CH$_2$CH(OH)CH$_2$OH | —N—Ac<br>\|<br>CH$_2$CH(OH)CH$_2$OH |

Among dimeric compounds of type (b), particularly preferred are those listed in Table 3.

TABLE 3

Preferred compounds of type (b)

| Generic Name (source) CAS [RN] | FORMULA II | | |
|---|---|---|---|
| | A | B=D | E—X—E |
| iofratol [141660-63-1] | —CONHCH(CH$_2$OH)$_2$ | —NHCOCH(OH)CH$_3$ | —CONHCH$_2$CHCH$_2$OH<br>\|<br>OH |
| iodixanol [92339-11-2] | —CONHCH$_2$CH(OH)CH$_2$OH | —CONHCH$_2$CH(OH)CH$_2$OH | —NCH$_2$CHCH$_2$N—<br>\| \| \|<br>Ac  OH  Ac |
| iotrol [79770-24-4] | —CONHCHCH(OH)CH$_2$OH<br>\|<br>CH$_2$OH | —CONHCHCH(OH)CH$_2$OH<br>\|<br>CH$_2$OH | —NCOCH$_2$CON—<br>\|          \|<br>Me        Me |
| iotasul [71767-13-0] | —CONCH$_2$CH(OH)CH$_2$OH<br>\|<br>Me | —CONCH$_2$CH(OH)CH$_2$OH<br>\|<br>Me | —NHCOCH$_2$CH$_2$<br>                          \\<br>                           S<br>                          /<br>—NHCOCH$_2$CH$_2$ |
| iodecol [81045-33-2] | —CONHCH(CH$_2$OH)$_2$ | —CONHCH(CH$_2$OH)$_2$ | —N—COCH$_2$CO—N—<br>\|                          \|<br>CH$_2$CH$_2$OH    CH$_2$CH$_2$OH |
| (WO 92/08691) [143200-04-8] | —CONHCH$_2$CH(OH)CH$_2$OH | —NHCOCH$_2$OH | —CONHCH$_2$CHCH$_2$NHCO—<br>\|<br>OH |
| (WO 92/08691) [143199-77-3] | —CONHCH(CH$_2$OH)$_2$ | —NHCOCH$_2$OH | —CONHCH$_2$CHCH$_2$NHCO—<br>\|<br>OH |
| (WO 92/08691) [143200-00-4] | —CONHCH$_2$CH(OH)CH$_2$OH | —NHCOCH$_2$OH | CH$_2$OH<br>\|<br>—CONHCH$_2$CCH$_2$NHCO—<br>\|<br>CH$_2$OH |
| (US 4348377) [78341-84-1] | —CONHCH$_2$CH(OH)CH$_2$OH (B 17500) | —CONHCH$_2$CH(OH)CH$_2$OH | —NCH$_2$CH$_2$CH$_2$N—<br>\|                \|<br>COCH$_2$OH  COCH$_2$OH |
| (EP 0308364) [122731-47-9] | —CONCH$_2$CH(OH)CH$_2$OH<br>\|<br>Me | —CONHCH$_2$CH(OH)CH$_2$OH | —NCOCH$_2$CON—<br>\|          \|<br>Me        Me |
| (EP 0308364) [122731-49-1] | —CONHCHCH(OH)CH$_2$OH<br>\|<br>CH$_2$OH | —CONHCH$_2$CH(OH)CH$_2$OH | —NCOCH$_2$CON—<br>\|          \|<br>Me        Me |
| (WO 85/01727) [99139-65-8] | —NCH$_2$CH(OH)CH$_2$OH<br>\|<br>Ac | —NCH$_2$CH(OH)CH$_2$OH<br>\|<br>Ac | —CONHCH$_2$CH$_2$NHCO— |

TABLE 3-continued

Preferred compounds of type (b)

| Generic Name (source) CAS [RN] | A | B = D | E—X—E |
|---|---|---|---|
| (WO 85/01727) [99139-62-5] | —NCH$_2$CH(OH)CH$_2$OH<br>\|<br>Ac | —NCH$_2$CH(OH)CH$_2$OH<br>\|<br>Ac | —CON—CH$_2$CH$_2$NHCO—<br>\|<br>CH$_2$CH$_2$OH |
| (EP 0023992) [78341-84-1] | —CONHCH$_2$CH(OH)CH$_2$OH | —CONHCH$_2$CH(OH)CH$_2$OH | —NCH$_2$CH$_2$CH$_2$N—<br>\|         \|<br>COCH$_2$OH  COCH$_2$OH |

Particularly preferred contrastographic compositions of this invention comprise the following iodinated monomer and dimer mixtures:

iopamidol/iofratol; iomeprol/iofratol; iomeprol/compound A [EP 23992 B: Ex.15]; iopamidol/compound A; iohexol/iodixanol; iopromide/iodecol; iopromide/iotrol; iomeprol/iodecol; iomeprol/iodixanol; iopentol/iodixanol and all their combinations.

In the compositions of this invention the respective proportions of compounds (a) and (b) can limitlessly vary within the range indicated in the claims (i.e. (a) and (b) are present in the mixture in such a ratio that the iodine quantity of (b) can range between 10–90% in weight, preferably between 20–75%, of the total iodine content in the composition, while the chosen values basically depend upon the specific diagnostic use and the desired properties of the injectable preparation. Some of them can be mentioned: iodine concentration, osmolality, viscosity, distribution flow in circulation or in other cavities, time of retention in the organs to be examined, excretion and ways of elimination. Specific data concerning the above mentioned parameters are reported in the following experimental examples.

The formulations of this invention, which mixture of opacifying agents (a) and (b) is totally dissolved to give iodine concentrations of 200–450 g/L or more, are particularly suitable for the anglographic imaging of small vessels, i.e. in brain and cerebrospinal cavities, requiring a low viscosity contrast liquid injection.

According to the use, viscosity can be kept between 4–12 mPa's, while osmolality can vary between 50–500 mosmol/kg. It was particularly surprising that the mixtures of compounds (a) and (b) according to the present invention showed a better tolerability—especially neurotropic—than the one expected by adding those of the single components. The reason for this unexpected remarkable advantage has no explanation yet.

The performance of the compositions of this invention is completed and increased by the addition of a series of additives, particularly stabilisers, agents controlling the dissolution, buffers (i.e. TRIS) or also biologically acceptable mineral salts.

The additives of the formulations of this inventions are those commonly known and used in the pharmaceutical technique.

As matter of non-limiting example, the following salts and compounds can be cited as particularly preferred additives: halides, carbonates, bicarbonates, sulphates, Na$^+$, Mg$_2^+$, Ca$^{2+}$, phosphates, tromethamol, EDTA, EDTA CaNa$_2$, heparin, hirudin, glycerol, polyethyleneglycol, dextran and the like.

During the preparation of the composition of this invention, the various ingredients are preferably gradually diluted into a suitable aqueous medium. One of the preferred procedure, for example, can be summed up as follows:

one or more iodinated compounds—monomers and dimers—are dissolved in distilled water in successive portions, with the possible addition of additives. The resulting solution is submitted to ultrafiltration by using a porously calibrated membrane, as described in the following examples. Then sterilisation is performed according to the standard methods used to prepare X-ray injectable contrast medium formulations.

Other aspect s of this invention are more extensively described in the following section.

EXAMPLE 1

An injectable contrastographic composition has been prepared by introducing into water the following ingredients: 246.3 g of iomeprol (0.324 mol), 342.2 g of iofratol (0.234 mol), 0.8 g of tromethamol, 0.36 g of concentrated HCl. The resulting solution has been firstly diluted to 1 L and then depyrogenated through ultrafiltration by using a cellulose membrane Amicon® Y10 (10000 Dalton) [temperature= 45±5° C.; loading pressure=5 kg/cm$^2$; permeate flow rate= 55 mL/s ]. Then, sterilisation is carried out for 30 min at 120° C. The resulting solution, containing 300 g of iodine per L, has been labelled as "iomeprol/iofratol 300". In a similar way another solution, labelled as "iomeprol/iofratol 320", has been prepared using 255.6 g of iomeprol (0.366 mol), 373.8 g of iofratol (0.256 mol), 0.79 g of tromethamol and 0.38 of concentrated HCl (iodine content=320 g/L).

In addition, two 1 L control solutions have been prepared. They contained 0.8 g of tromethamol and 0.36 mg of HCl in addition to the following contrastographic agents:

1° labelled as: "iofratol 300", containing 576.1 g/L of iofratol
2° labelled as: "iomeprol 350", containing 714.4 g/L of iomeprol.

The intracerebral toxicity of the previous solution has been determined by using mice of both sexes, carrying out the experimental protocol described in J. T. Litchfield et al., Pharmacol. Exp. Ther. 96 (1949), 99.

LD$_{50}$ values, expressed in g (iodine)/kg, were the following:

| iomeprol/iofratol 300 | > 1.5 |
| iomeprol/iofratol 320 | > 1.6 |
| iomeprol 350 | = 1.30 (1.18–1.44) |
| iofratol 300 | = 0.65 (0.57–0.73) |

As clearly shown by the previous data, LD$_{50}$ values in iomeprol/iofratol mixtures were surprisingly higher than those foreseable from the two control solutions. Unfortunately, the exact values were not determined, since higher volumes could not be technically administered to animals.

EXAMPLE 2

A solution of iomeprol/iofratol 300 (1 L) is prepared according to the procedure described in Example 1.

This solution has a newtonian hydrodynamic behaviour, a viscosity value (measured at 37° C.) of 6.24 mPa's and osmolality of about 300 mosmol/kg (osmometric method of vapour pressure).

The iodine delivery rate Q (expressed in g of iodine/s) is measured by means of a 6 hole, 90-cm pigtail Cordis® 4F catheter at a temperature of 37° C. and at a pressure of about 58.5 atm or 5.92 mPa. In the same way, Q values are measured in control solutions of iomeprol 300 and iofratol 300. The resulting values are reported in the following table:

| Solution | Q g (iodine)/s | Osmolality (mosmol/kg) |
|---|---|---|
| iomeprol/iofratol 300 | 3.79 | 300 |
| iomeprol 300 | 4.13 | 517 |
| iofratol 300 | 3.43 | 141 |

When compared to pure compound solutions, the advantages of the mixture are striking: osmolality is practically equivalent to blood, while the catheter flow rate is higher than the pure dimeric and a bit lower than the pure monomeric, which is greatly hyperosmolal.

EXAMPLE 3

A solution (1 L) containing a mixture of 178.12 g of iomeprol (0.234 mol) and 596.35 g of iofratol (0.408 mol) is prepared according to the procedure described in Example 1.

The resulting solution (labelled as "iomeprol/iofratol 400") has a iodine content of 400 g (iodine)/L.

The two control solutions are prepared according to the procedure of Example 1:

"iomeprol 400": 798.95 g of iomeprol in 1 L of solution (400 g (iodine)/L)

"iofratol 400": 767.45 g of iofratol in 1 L of solution (400 g (iodine)/L).

The viscosity of the three solutions is measured at 37° C. by means of a Haake CV100 viscometer. The results obtained (iomeprol/iofratol 400=14.3 mPa's; iomeprol 400= 13.6 mPa's; iofratol 400=30.8 mPa's) show that the mixture viscosity is surprisingly similar to the one of the less viscous component (the monomer), taken alone, and lower than the one calculated by hypothesizing the contribution of the two components proportional to their presence in the mixture in molar fraction terms.

EXAMPLE 4

Further compositions were prepared according to the invention, by using the pair of compounds hereunder listed, in concentrations that allowed solutions at a iodine content of about 300 g (iodine)/L. The component ratio has been studied case by case to obtain a osmolal value similar to blood for each formulation.

The following mixtures have been prepared confirming the previously discussed unexpected advantages, in comparison to the solutions of each single component with the same iodine content of the mixture:
iohexol/iodixanol; iopromide/iodecol; iopromide/iotrol; iomeprol/iodecol; iomeprol/iodixanol; iopentol/iodixanol.

We claim:

1. An aqueous injectable composition, useful to obtain images during X-ray examinations, comprising, dissolved into an aqueous medium, a mixture of:

(a) a non-ionic organic compound comprising a triiodinated aromatic nucleus having, in the remaining positions, linear or branched functionally substituted organic residues, said compound (a) having formula

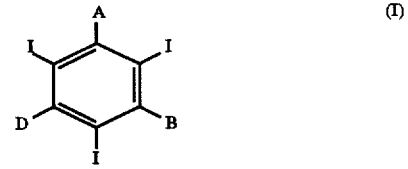

wherein:

A, B, D are the same or different and are —CON(R)R$_1$ or —N(R)—CO—R$_2$ groups wherein R is H or a linear or branched alkyl residue (C$_1$–C$_6$), unsubstituted or substituted by 1–5 OH alkoxy or hydroxyalkoxy groups, or both OH and alkoxy or both OH and hydroxyalkoxy groups, R$_1$ is a linear or branched alkyl residue (C$_1$–C$_6$), unsubstituted or substituted by 1–5 OH or alkoxy, OH and hydroxyalkoxy groups, or both OH and alkoxy or both OH and hydroxyalkoxy groups, or by one of the groups —NH—CO—R$_1$ or —CO—N(R)R$_1$, or R$_1$ is the residue of a carbohydrate, or R$_1$ and R, taken together, are an alkylene chain (C$_3$–C$_7$), said alkylene chain being non-interrupted or interrupted by O, S, N, or an oxo group, R$_2$ is a linear or branched alkyl residue (C$_1$–C$_6$), unsubstituted or substituted by 1–5 OH or alkoxy or hydroxyalkoxy groups, or both OH and alkoxy, OH and hydroxyalkoxy groups, (b) is a non-ionic organic compound comprising at least two triiodinated aromatic nuclei covalently bound together, in one of the non iodine-substituted positions through a linear or branched and functionally substituted organic residue, said aromatic nuclei being further substituted in the remaining positions by organic residues as defined hereinabove in compound (a), said compound (b) having the formula (II)

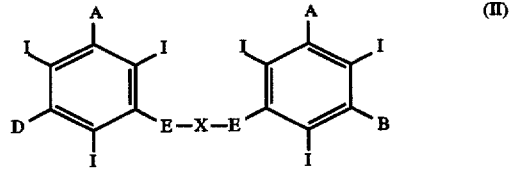

wherein:

A, B, D, are the same or different, and have the same meaning as in formula (I), E, are the same or different, and are a member selected from the group consisting of —CO—N(R)—, —N(R)—CO—, —N(COR$_3$)— wherein R has the same meaning as in formula (I) and R$_3$ is an alkyl residue (C$_1$–C$_3$) which is unsubstituted or substituted by 1–2 OH or by alkoxy or hydroxyalkoxy groups, X is a covalent bond or a linear or branched alkylene chain ($C_1$–$C_8$), which is unsubstituted or substituted by 1–6 OH groups or —CO—NHR groups, or both OH and —CO—NHR groups, said alkylene chain being non-interrupted or interrupted by —O—, —S—, —N—, —N(R)—CO groups, R being the same as in formula (I), said compounds (a) and (b) being present in said mixture in such a ratio that the iodine quantity of compound (b) ranges between 10 and 90% by weight of the total iodine amount present in the composition, and the total iodine amount in the composition ranges from 200 to 450 g I/l, said composition further having an osmolality 0.8–1.5 times the physiological value and a viscosity ranging from 4 to 12 mPa's.

2. The composition according to claim 1, wherein said compound (a) is a member selected from the group consisting of iopamidol, metrizamide, iodamide, iomeprol, iopromoide, ioversol, ioglunide, iosimide, iohexol, iogulamide and said compound (b) is a member selected from the group consisting of iotrolan, iodixanol, iofratol, 1,3-bis-[N-(3,5-bis-(2,3,-dihydroxypropyl-aminocarbonyl)-2,4,6-triiodophenyl)-N-hydroxyacetyl-amino]-propane.

3. The composition according to claim 1 which comprises additives selected from excipients, stabilizers, control agents for dissolution, physiologically tolerable water-soluble mineral salts, wherein said mineral salts are halides, carbonates, bicarbonates, sulphates, phosphates of Na, K, Mg, Ca and an anticlotting agent which is heparin or hirudin.

4. The composition according to claim 3 wherein said excipients are glycerol, polyethylenglycol or dextran.

5. The composition according to claim 3 wherein said stabilizers are tromethamol, EDTA, EDTA $CaNa_2$, or sodium phosphate.

* * * * *